(12) United States Patent
Sellers et al.

(10) Patent No.: US 12,239,764 B2
(45) Date of Patent: Mar. 4, 2025

(54) URINARY CATHETERS WITH IMPROVED SHAPE RECOVERY AND EASE OF USE

(71) Applicant: Hollister Incorporated, Libertyville, IL (US)

(72) Inventors: Brent H. Sellers, Libertyville, IL (US); Paul Healy, Claremorris (IE); William K. Arnold, Gurnee, IL (US); Horacio Montes De Oca Balderas, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 17/906,038

(22) PCT Filed: Mar. 11, 2021

(86) PCT No.: PCT/US2021/021821
§ 371 (c)(1),
(2) Date: Sep. 9, 2022

(87) PCT Pub. No.: WO2021/183718
PCT Pub. Date: Sep. 16, 2021

(65) Prior Publication Data
US 2023/0138293 A1    May 4, 2023

Related U.S. Application Data

(60) Provisional application No. 62/989,277, filed on Mar. 13, 2020.

(51) Int. Cl.
| | | |
|---|---|---|
| *A61M 25/00* | (2006.01) | |
| *A61L 2/08* | (2006.01) | |
| *A61L 2/26* | (2006.01) | |
| *A61L 29/06* | (2006.01) | |

(52) U.S. Cl.
CPC ............... *A61L 29/06* (2013.01); *A61L 2/087* (2013.01); *A61L 2/26* (2013.01); *A61M 25/0009* (2013.01); *A61M 25/002* (2013.01); *A61L 2202/18* (2013.01); *A61L 2202/24* (2013.01); *A61L 2400/10* (2013.01); *A61L 2400/16* (2013.01); *A61M 2205/0222* (2013.01)

(58) Field of Classification Search
CPC . A61M 25/002; A61M 25/0009; A61L 29/06; A61L 2/087; A61L 2/26
USPC ......................................... 206/210, 363, 438
See application file for complete search history.

(56) References Cited

U.S. PATENT DOCUMENTS

| | | |
|---|---|---|
| 5,312,356 A | 5/1994 | Engelson et al. |
| 5,944,701 A | 8/1999 | Dubrul |
| 7,951,115 B2 | 5/2011 | Altman |
| | (Continued) | |

FOREIGN PATENT DOCUMENTS

| | | |
|---|---|---|
| EP | 0328421 A2 | 8/1989 |
| EP | 0588546 A2 | 3/1994 |
| | (Continued) | |

OTHER PUBLICATIONS

International Search Report and Written Opinion for PCT/US2021/021821 Dated Sep. 9, 2021.

*Primary Examiner* — Steven A. Reynolds
(74) *Attorney, Agent, or Firm* — Cook Alex Ltd.

(57) ABSTRACT

Catheters including thermoplastic polyurethane polymer tubing with improved shape recovery after storage in a substantially coiled configuration are provided.

16 Claims, 3 Drawing Sheets

(56) References Cited

U.S. PATENT DOCUMENTS

| | | |
|---|---|---|
| 8,123,739 B2 | 2/2012 | McQueen |
| 8,328,791 B2 | 12/2012 | Griffin |
| 8,377,559 B2 | 2/2013 | Gilman |
| 8,945,110 B2 | 2/2015 | Fish et al. |
| 9,168,353 B2 | 10/2015 | Chambers |
| 9,821,142 B2 | 11/2017 | Hannon et al. |
| 9,867,907 B2 | 1/2018 | Rostami et al. |
| 9,925,355 B2 | 3/2018 | Foley et al. |
| 10,029,071 B2 | 7/2018 | Hannon et al. |
| 10,434,282 B2 | 10/2019 | Kearns et al. |
| 11,707,289 B2 | 7/2023 | McCaffrey |
| 11,826,065 B2 | 11/2023 | Bashir |
| 2006/0025753 A1 | 2/2006 | Kubalak et al. |
| 2008/0125757 A1* | 5/2008 | Gobel .................... A61M 25/04 |
| | | 604/544 |
| 2008/0172037 A1 | 7/2008 | Huang et al. |
| 2008/0281291 A1* | 11/2008 | Tihon ................ A61M 25/0017 |
| | | 604/517 |
| 2011/0190683 A1 | 8/2011 | Gellman |
| 2012/0123328 A1 | 5/2012 | Williams |
| 2012/0165956 A1 | 6/2012 | Li |
| 2016/0038713 A1* | 2/2016 | Kearns ............... A61M 25/0111 |
| | | 206/364 |
| 2016/0263285 A1 | 9/2016 | Rostami et al. |
| 2017/0216558 A1 | 8/2017 | Hughett et al. |
| 2018/0001055 A1 | 1/2018 | Utas et al. |
| 2018/0117288 A1 | 5/2018 | Lindsay et al. |
| 2018/0126035 A1* | 5/2018 | O'Mahony .......... C10M 107/22 |
| 2022/0226607 A1 | 7/2022 | Bishawi |

FOREIGN PATENT DOCUMENTS

| | | |
|---|---|---|
| EP | 2774648 A1 | 9/2014 |
| EP | 2946803 B1 | 11/2015 |
| EP | 2967968 A1 | 1/2016 |
| EP | 3283136 A1 | 2/2018 |
| EP | 3590573 A1 | 1/2020 |
| JP | H05154192 A | 6/1993 |
| WO | 2004056414 A1 | 7/2004 |
| WO | 2008155145 A1 | 12/2008 |
| WO | 2023076162 A1 | 5/2023 |

* cited by examiner

URINARY CATHETERS WITH IMPROVED SHAPE RECOVERY AND EASE OF USE

CROSS-REFERENCE TO RELATED APPLICATION

The present application is the U.S. National Stage Application of PCT Application No. PCT/US2021/021821, filed Mar. 11, 2021, which claims the benefit of U.S. Provisional Patent Application Ser. No. 62/989,277, filed Mar. 13, 2020, the disclosure of all of which is hereby incorporated by reference in its entirety.

DESCRIPTION

Technical Field

The present disclosure generally relates to catheters comprised of a thermoplastic polyurethane, and more particularly, for catheters with thermoplastic polyurethane polymer tubing that have a high percentage of recovery after storage in a coiled configuration.

Background

Catheters are used to treat many different types of medical conditions and typically include an elongated catheter shaft that is inserted into and through a passageway or lumen of the body. Catheters, and in particular intermittent catheters, are commonly used by those who suffer from various abnormalities of the urinary system, such as urinary incontinence.

Urinary catheters generally comprise a catheter shaft. The catheter shaft includes a proximal end having a tip that is inserted into and through a user's urethra. The catheter shaft also includes a distal end that includes a drainage member, which may be a funnel or connector that facilitates drainage of bodily fluids for the catheter shaft.

For discreet storage and carrying, it may be desirable to store catheters in a package in a coiled or circular configuration. The catheter assembly is packaged, sterilized and stored for a number of days to months, before use. Oftentimes, after removal from the packaging, the catheter undesirably retains its coiled shape, and it may take time and effort for the catheter to recover to its pre-coiled shape. This can be especially troublesome for users that have limited dexterity.

For various reasons, including but not limited to efficiency, effectiveness and ease of use, it is desirable to provide a catheter tubing material with a higher percentage recovery after storage in a substantially coiled configuration.

Therefore, there remains a need for catheters that have sufficient shape recovery.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a catheter product includes a package defining a cavity and a catheter including a thermoplastic polyurethane polymer tubing contained within the cavity of the package, wherein at least a portion of the tubing is in a substantially arcuate configuration within the cavity. The portion of the polymer tubing is defined between a proximal location on the polymer tubing and a distal location on the polymer tubing. The portion of the polymer tubing has a shape recovery after 1 month at room temperature of at least 35%. The percent shape recovery of the portion of the tubing is calculated by the formula: percent shape recovery=$[1-(L0-L2)/(L0-L1)] \times 100$, where L0 is the length of the portion of the polymer tubing as measured from the proximal location to the distal location when in a straight configuration, L1 is the diameter of curvature of the portion of the tubing when in the arcuate configuration within the cavity, and L2 is the distance between the proximal location and distal location of the portion of the tubing after removal from the arcuate configuration.

In another aspect, a method for making a urinary catheter product with improved shape recovery includes annealing a thermoplastic polyurethane tubing of a catheter for at least 2 hours at 100 C and placing the catheter in a substantially arcuate configuration within a cavity of a package, wherein at least a portion of the tubing is in a substantially arcuate configuration within the cavity, the portion of the polymer tubing being defined between a proximal location on the tubing and a distal location on the tubing. The portion of the polymer tubing has a shape recovery after 1 month at room temperature of at least 35%. The percent shape recovery of the portion of the tubing is calculated by the formula: percent shape recovery=$[1-(L0-L2)/(L0-L1)] \times 100$, where L0 is the length of the portion of the polymer tubing as measured from the proximal location to the distal location when in a straight configuration, L1 is the diameter of curvature of the portion of the tubing when in the arcuate configuration within the cavity, and L2 is the distance between the proximal location and distal location of the portion of the tubing after removal from the arcuate configuration.

In another aspect, an intermittent urinary catheter includes a thermoplastic polyurethane polymer tubing wherein at least a portion of the tubing has an initial straight configuration, a substantially arcuate configuration, and a recovery configuration. The portion of the polymer tubing is defined between a proximal location of the tubing and a distal location of the tubing. The recovery configuration has a shape recovery after being in the arcuate configuration for 1 month at room temperature of at least 35%. The percent shape recovery of the portion of the tubing is calculated by the formula: percent shape recovery=$[1-(L0-L2)/(L0-L1)] \times 100$, where L0 is the length of the portion of the polymer tubing as measured from the proximal end to the distal end when in a straight configuration, L1 is the diameter of curvature of the portion of the tubing when in the arcuate configuration, and L2 is the distance between the proximal location and distal location of the tubing after removal from the arcuate configuration and in the recovery configuration.

In another aspect, a catheter product includes a package defining a cavity and a catheter including a thermoplastic polymer tubing contained within the cavity of the package, wherein at least a portion of the tubing is in a substantially arcuate configuration within the cavity. The portion of the polymer tubing is defined between a proximal location on the polymer tubing and a distal location on the polymer tubing. The portion of the polymer tubing has a shape recovery after 1 month at room temperature of at least 35%. The percent shape recovery of the portion of the tubing is calculated by the formula: percent shape recovery=$[1-(L0-L2)/(L0-L1)] \times 100$, where L0 is the length of the portion of the polymer tubing as measured from the proximal location to the distal location when in a straight configuration, L1 is the diameter of curvature of the portion of the tubing when in the arcuate configuration within the cavity, and L2 is the distance between the proximal location and distal location of the portion of the tubing after removal from the arcuate configuration. The storage modulus (E') of the polymer tubing is greater than or equal to 19 MPa and less than or equal to 50 MPa and the loss modulus (E") of the polymer tubing is greater than or equal to 2.8 MPa and less than or equal to 8.9 MPa.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present disclosure is directed to catheters that include tubing that may be inserted into and advanced within a lumen of a body, such as a urethra.

The catheters of the present disclosure include tubing that is made from a polymer material(s). The polymer material can be polyurethane, specifically a thermoplastic polyurethane. Thermoplastic polyurethanes can be polyester, polyether, or polycaprolactone based and can be aromatic or aliphatic. One or more of these thermoplastic polyurethanes may be utilized in the current embodiments. In an embodiment according to the current disclosure, the thermoplastic polyurethane is an aromatic polyether thermoplastic polyurethane. Blends of different thermoplastic polyurethanes or blends of different polymers, including polymers such as polyvinyl chloride (PVC) and thermoplastic elastomers (TPE) may also be used.

The shore hardness of the polymer tubing may be in the range of 80 A-95 A, preferably at least 80 A, or at least 88 A, or at least 90 A. In one embodiment, the shore hardness is in the range of 88 A-91 A. Hardness is calculated per the ASTM D2240 test method and tested with a durometer.

Figure 1:
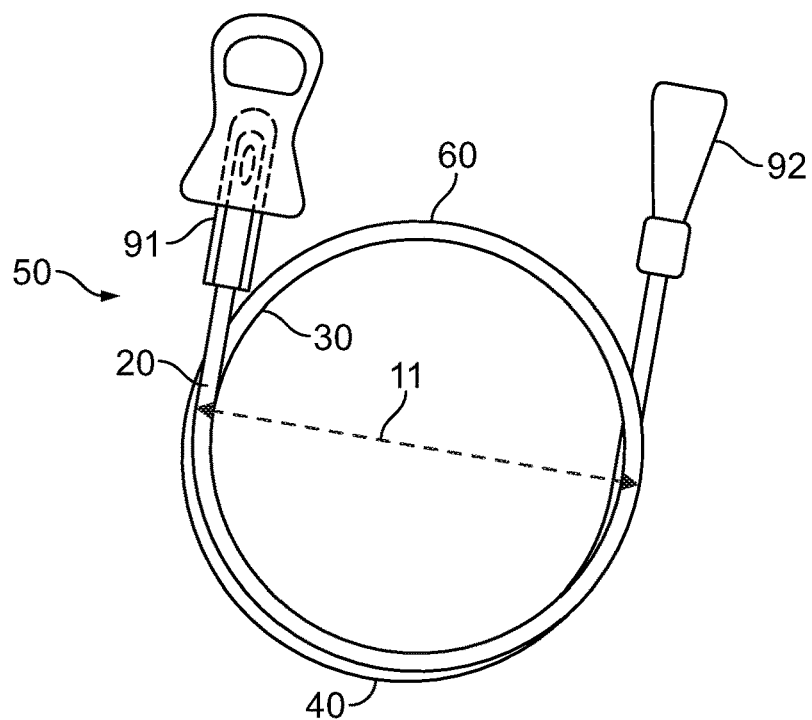
FIG. 1 includes a top view of a catheter according to one embodiment of the current disclosure.

FIG. 1 illustrates a urinary catheter 50 having catheter polymer tubing 60 made from any of the above-discussed polymers. Catheter tubing 60 may have an arcuate configuration, such as a coiled, wound, bent or curved configuration. In the coiled configuration, the catheter may be in a circular, oval or elliptical configuration. For example, the catheter tubing 60 may be wound or coiled into the coiled configuration shown in FIG. 1. The catheter 50 may be any suitable urinary catheter used for bladder drainage. The catheter 50 has a proximal end 91 which can include an introducer tip for insertion and a distal end 92 which can include a drainage member or funnel. In the illustrated embodiment, catheter 50 includes catheter tubing 60 having a portion 40 defined between a proximal location 20 and a distal location 30. Portion 40 has a diameter of curvature 11.

The catheter 50 may be a hydrophilic catheter and catheter tubing 60 may include a hydrophilic coating. When the hydrophilic coating is wetted or hydrated with a hydration medium, such as water, it becomes lubricious which eases introduction of the device into the body and aids in reducing pain and discomfort associated with such introduction. The hydrophilic coating can be a single layer or multilayer hydrophilic coating. Multiple layered coating can include at least a base coat and top layer.

Catheter 50, optionally, also may include a thin flexible sleeve that covers at least a section of the outer surface of the catheter tube 60. The sleeve may be formed of any variety of thin flexible polymeric film materials, such as polyethylene, plasticized PVC, polypropylene, polyurethane or elastomeric hydrogels. When catheter tube 16 includes a hydrophilic coating thereon, the sleeve may be liquid and/or vapor permeable so as to allow liquid and/or vapor therethrough to hydrate the hydrophilic coating while catheter 50 is stored within package 80. Alternatively, the sleeve may include a hydration liquid or a foamed hydration liquid within the sleeve and in contact with the hydrophilic material.

Figure 2:
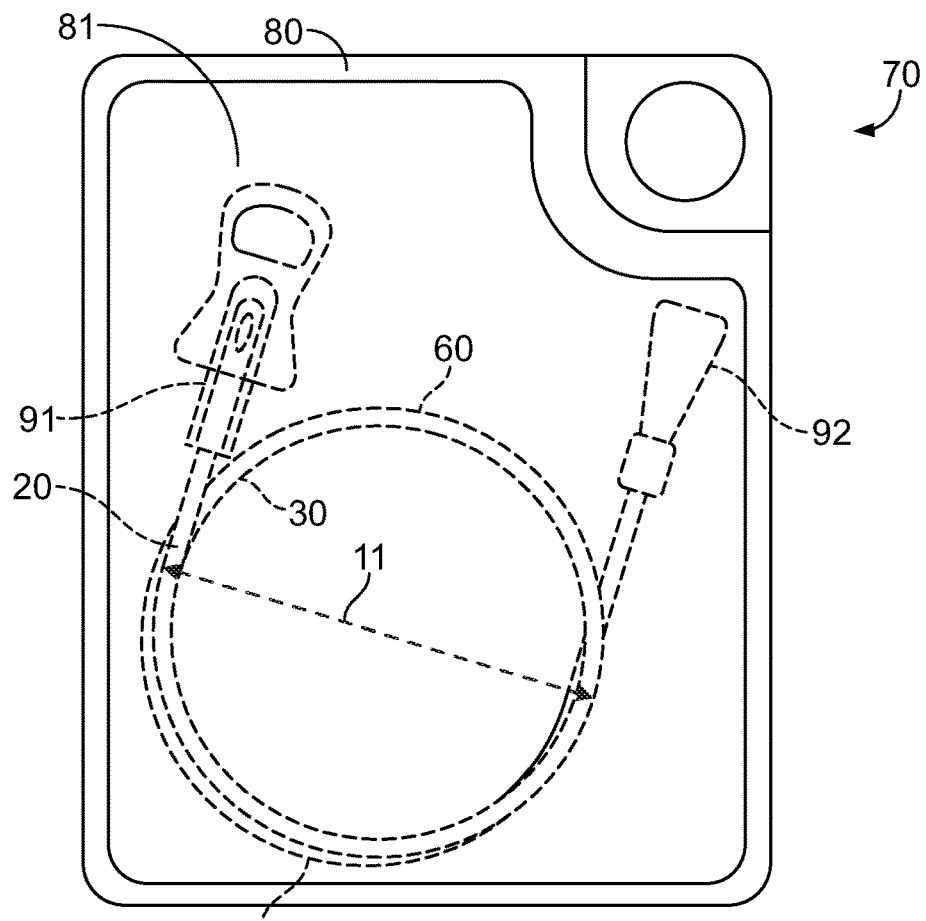
FIG. 2 includes a top view of a catheter product according to one embodiment of the current disclosure.

The urinary catheter may be part of a catheter product that includes a package 70 as shown in FIG. 2. Catheter package 70 includes catheter 50 within a cavity 81 of package 80. Wound or coiled catheter tube 60 may be single or multiply wound or coiled, depending on the size of the package and the type of catheter. Male urinary catheters typically have longer tubing, while female urinary catheters are typically short. An example of a longer catheter tubing and its packaging are included in FIGS. 1 and 2. An example of a shorter catheter tubing and its packaging are included in FIGS. 3 and 4.

Package 80 is preferably liquid and gas impermeable and may be made from any suitable liquid and gas impermeable materials, such as foils, polymers or multilayer films or laminates containing layers of metallic and/or polymer materials. In one embodiment, the package is made from aluminum foil. In another embodiment, the package is made from a polymer film. In yet another embodiment the package is made from a multilayered film including a polymer overlaying a foil, such as polypropylene covered aluminum foil.

In the embodiment illustrated in FIG. 2, package 80 is generally rectangular. The package also may be shapes other than rectangle. For example, the package 80 may be generally round (e.g. circular, oval, ellipse, etc.) or generally square.

When catheter 50 is a hydrophilic catheter, package 80 may include one or more sources for hydrating the hydrophilic surface of the catheter while the catheter is stored within the package. An amount of hydration liquid, or wetting fluid, for contacting and hydrating the hydrophilic surface of the catheter 50 may be contained (or provided) within cavity 81 of package 80. In an alternative embodiment, an amount of vapor donating liquid that provides a hydration vapor for vapor hydrating the hydrophilic surface of the catheter 50 may be disposed within cavity of package 80. The hydration liquid, or wetting fluid, may include water and a number of additives. Additives can include stability compounds or antioxidants including, but not limited to, glycerol, topherols, and ascorbic acid.

Figure 3:
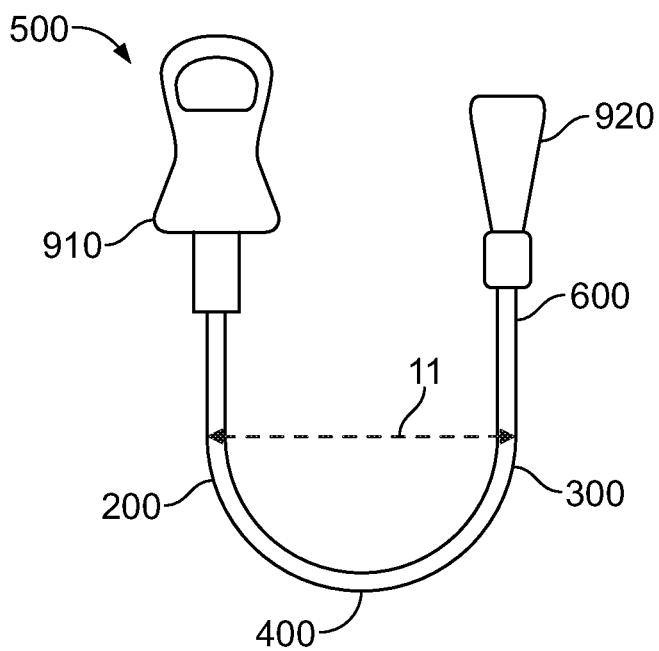
FIG. 3 includes a top view of a catheter according to one embodiment of the current disclosure.
Figure 4:
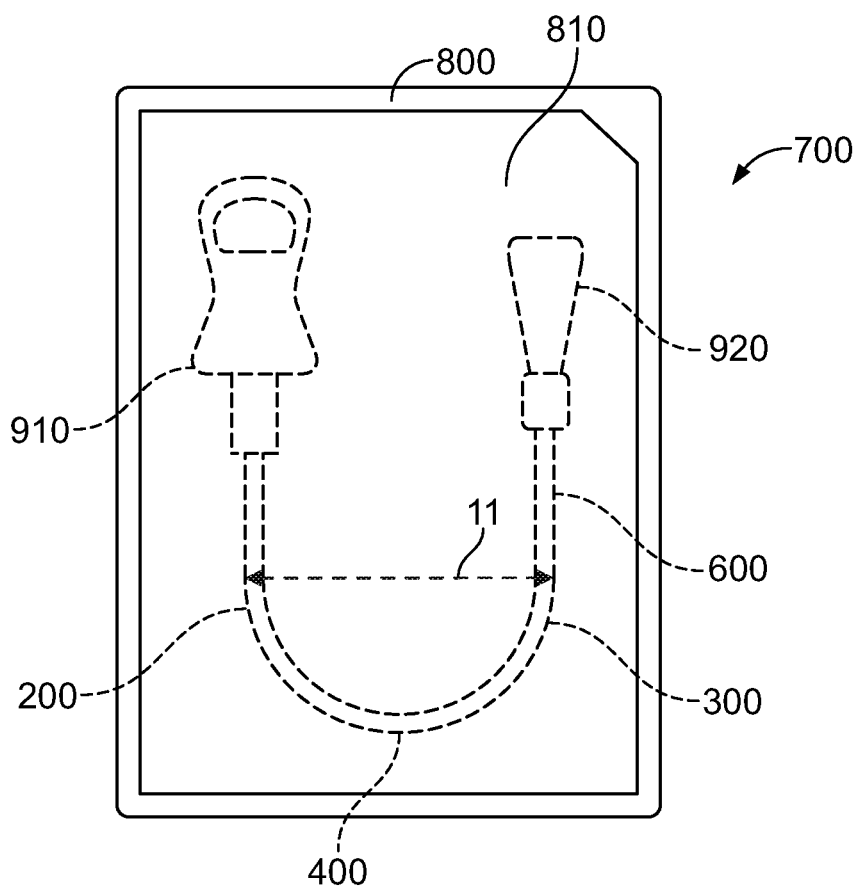
FIG. 4 includes a top view of a catheter product according to one embodiment of the current disclosure.

FIGS. 3 and 4 show a shorter length catheter 500 and a catheter package 700. Catheter 500 may have the same features as catheter 50 disclosed above except that it is much shorter in length because it is designed to be used by females (who have a much shorter urethra than males). Packaging 800 may have the same features as package 80 as described above. In this embodiment, catheter 500 has an arcuate configuration, such as a compact bent, curved or arcuate configuration, when placed within cavity 810 of the package 800. The catheter 500 has a proximal end 910 for insertion and a distal end 920 which can include a drainage member or funnel. In the illustrated embodiment, catheter 500 includes an elongated catheter tube 600 having a portion 400 between a proximal location 200 and a distal location 300. Portion 400 has a diameter of curvature 11.

The catheters and/or catheter tubing of the current disclosure may be annealed to improve characteristics of the polymer tubing. Annealing is a heating process used to alter the characteristics of a compound. According to some embodiments of the current disclosure, the catheter and/or catheter tubing may be annealed for at least 2 hours at 100 C. In additional embodiments, the catheter and/or catheter tubing may be annealed for at least 20 hours at 100 C.

The catheters and catheter packages of the present disclosure may be sterilized prior to use. The catheter packages may be sterilized by applying a sufficient amount of radiation, such as gamma or E-Beam radiation. In one embodiment, the packages are electron beam sterilized at 10 MeV with a dose in the range of 25-65 kGy. The catheter packages can be sterilized with radiation while the hydrophilic coating is in contact with the wetting fluid.

Figure 5:
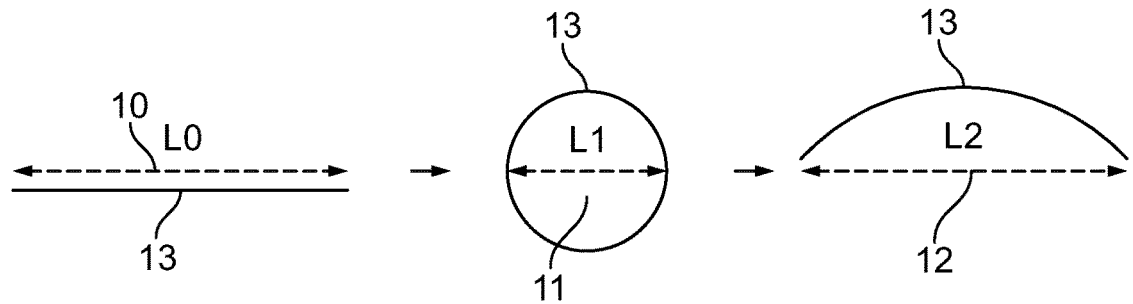
FIG. 5 includes a schematic illustration of dimensional measurements for calculating percent recovery.

FIG. 5 illustrates the dimensional measurement for calculating percent recovery for a portion of catheter tubing. A portion 13 of the catheter, which may be the entire catheter tubing or a portion of the catheter tubing, has an initial length 10, L0, as measured from a proximal location to a distal location when in a straight configuration. In the arcuate configuration, such as in a coiled configuration, after packaging, the portion 13 has a diameter of curvature 11, L1. As shown in FIGS. 1 and 3, the portion can form a coiled or curved configuration. Additionally, the portion can form any shape with a curved portion, including, but not limited to, an oval or ellipse. When the coil is a substantially circular configuration, the diameter of curvature may be the diameter of the substantially circular configuration. When the tube is in curved configurations, the diameter of curvature may be the major or minor axis of the curved configuration. After removal from the arcuate configuration, the portion 13 has a distance L2 between the proximal location and distal location.

EXAMPLES

Example 1

Thermoplastic Urethane (TPU, Pellethane®), Polyvinyl Chloride (PVC), and Styrene-Ethylene-Butylene-Styrene/Polypropylene (SEBS/PP) Based Thermoplastic Elastomer (TPE) CH14 catheter tubing materials of different shore hardness (A) were packed in coiled configurations with three different lengths of the portion of the polymer tubing as measured from the proximal location to the distal location when in a straight configuration (L0=78.5, 122, and 166.5). The tubing material was fastened in the coiled configuration. Prior to packing, some samples were annealed (indicated by ann). Annealing was carried out at 100° C. for 20 hours in a vertical position with a metal rod inside the lumen of the tube, the rod had a diameter smaller than the inner diameter of the tubing. Approximately 4 mL of water was added to each pack. Each pack was sealed and electron beam sterilized at 10 MeV with a dose in the range of 25-65 kGy. The packs were stored for 1 month at room temperature. After 1 month, the samples were freely hung for 2 minutes and then the length of the partially curved catheter portion (L2) measurement was taken.

Percent recovery was calculated using the formula: percent recovery=$[1-(L0-L2)/(L0-L1)] \times 100$. Where L0 is the length of the portion of the polymer tubing as measured from the proximal location to the distal location when in a straight configuration, L1 is the diameter of curvature of the portion of the tubing when in the coiled configuration within the cavity, and L2 is the distance between the proximal location and distal location of the portion of the tubing after removal from the coiled configuration.

Table 1 shows the % recovery for L0=78.5 mm.

TABLE 1

| Material | L1 | L2 | % recovery |
|---|---|---|---|
| Pellethane 2363-90AE | 52.0 | 64.3 | 46 |
| Pellethane 2363-90AE ann. | 51.0 | 70.1 | 69 |
| Pellethane 2363-80AE | 51.0 | 68.5 | 64 |
| Pellethane 2363-80AE ann. | 52.0 | 70.5 | 70 |
| PVC 82A | 51.0 | 60.0 | 33 |
| TPE 83A | 49.0 | 65.5 | 56 |

Table 2 shows the % recovery for L0=122 mm.

TABLE 2

| Material | L1 | L2 | % recovery |
|---|---|---|---|
| Pellethane 2363-90AE | 78 | 96 | 41 |
| Pellethane 2363-90AE ann | 77 | 110 | 73 |
| Pellethane 2363-80AE | 78 | 104 | 59 |
| Pellethane 2363-80AE ann | 79 | 112 | 77 |
| PVC 82A | 77 | 91 | 31 |
| TPE 83A | 77 | 101 | 53 |

Table 3 shows the % recovery for L0=166.5 mm.

TABLE 3

| Material | L1 | L2 | % recovery |
|---|---|---|---|
| Pellethane 2363-90AE | 107 | 137 | 50 |
| Pellethane 2363-90AE ann | 106 | 150 | 73 |
| Pellethane 2363-80AE | 112 | 147 | 64 |
| Pellethane 2363-80AE ann | 106 | 157 | 85 |
| PVC 82A | 112 | 135 | 42 |
| TPE 83A | 103 | 134 | 49 |

Example 2

Polyvinyl Chloride (PVC), Thermoplastic Elastomer (TPE), and polyolefin based elastomers (TPO) CH14 tubing materials of different shore hardness (A) were packed in coiled configurations in a medium package (L1=122). The tubing material was coiled in the package. Approximately 4 mL of water was added to each pack. Each pack was sealed and electron beam sterilized at 10 MeV with a dose in the range of 25-65 kGy. The packs were stored for 4 months at room temperature. L2 was measured after removal from the coiled configuration. Table 4 shows the percent recovery for each catheter tube.

TABLE 4

| Material | Recovery [%] |
|---|---|
| PVC 82A | 26 |
| PVC 91A | 14 |
| TPO 80A | 10 |
| TPO 90A | 10 |
| TPE 83A | 26 |
| TPE 90A | 14 |

Example 3

Different TPU (including commercially available Texin® and Pellethane®), PVC, and TPE CH14 tubing materials of varying shore hardness (A) were packed in coiled configurations with L0=141 mm. The tubing material was placed in a coiled metal jig that had a circular channel. The tubing material was placed in the channel of the jig, such that the channel held the tubing in the circular configuration. TPU samples were annealed. Annealing was carried out at 100° C. for 2 hours or 20 hours in a vertical position with a metal rod inside the lumen of the tube, the rod had a diameter smaller than the inner diameter of the tubing.

The tensile storage modulus (E') and loss modulus (E") was measured in the temperature range −60° C. to 70° C. at 1 Hz approximately 7 days after annealing. For viscoelastic materials, the storage modulus is proportional to the stored energy for the elastic portion of the material, and the loss modulus is proportional to the energy dissipated as heat for the viscous portion of the material. A Dynamic Mechanical Analyzer TA Instruments DMA Q800, available from TA Instruments, Inc., of New Castle, Del.; equipped with a film clamp and Thermal Advantage DMA Q800 V7.5 Build 127 software for data acquisition was used for measuring the storage modulus (E') and loss modulus (E"). The test parameters that were used include: frequency of 1 Hz, oscillation amplitude of 25.0, static force of 0.0100 N, force track at 125.0% and minimum oscillation force at 0.02000 N. The catheter tubing was cut into a 33 mm long section. That section was bisected along its axis. One half of the bisected tubing, having a length of 33 mm and a width of 6.5 mm, was used as the sample for the testing. The mechanical properties were then analysed using the instruments described above with the multi-frequency strain experimental program method. The experimental method steps include: turning data storage off, equilibrating at −65° C., maintaining isothermal state for 5 minutes, turning data storage on, and ramping temperature 2° C./min to a temperature of 70° C. The program halts and saves the collected data once the temperature of 70° C. has been reached during the temperature ramp step.

Tube samples were stored in the coiled shape for 6 weeks at 40° C. Samples were removed from the oven and equilibrated at room temperature for a minimum of 1 hour prior to uncoiling and taking the L2 measurement. Table 5 shows the percent recovery and storage modulus.

TABLE 5

| Material | L0 | L1 | L2 | % recovery | E' [MPa] | E" [MPa] |
|---|---|---|---|---|---|---|
| Pellethane 2363-90AE not ann | 141 | 90 | 109 | 37 | 26 | 5.1 |
| Pellethane 2363-90AE ann 2 h | 141 | 90 | 115 | 49 | 19 | 2.8 |
| Pellethane 2363-90AE ann 20 h | 141 | 90 | 116 | 51 | 19 | 2.8 |
| Texin 50D not ann | 141 | 90 | 100 | 19 | 75 | 19.8 |
| Texin 50D ann 2 h | 141 | 90 | 109 | 37 | 60 | 12.1 |
| Texin 50D ann 20 h | 141 | 90 | 110 | 39 | 50 | 8.9 |
| PVC91A | 141 | 90 | 95 | 10 | 41 | 17.5 |
| TPE 88A | 141 | 90 | 106 | 31 | 44 | 9.7 |

Example 4

PVC with shore hardness 91 A, TPE with shore hardness 88 A, and TPU with shore hardness 90 A Ch 14 catheter tubing was packed in three different pack sizes to compare the shape recovery between materials and pack designs. The tubing material was coiled in the pack. The packs were stored for a month at room temperature. Table 6 shows the pack dimensions with different length to width ratios. For this example, L0 was 40 cm and L1 corresponds to the width of the pack.

TABLE 6

| | Width [mm] | Length [mm] | Length/width [%] |
|---|---|---|---|
| Pack A | 105 | 140 | 75 |
| Pack B | 100 | 150 | 66 |
| Pack C | 70 | 160 | 44 |

Figure 6:
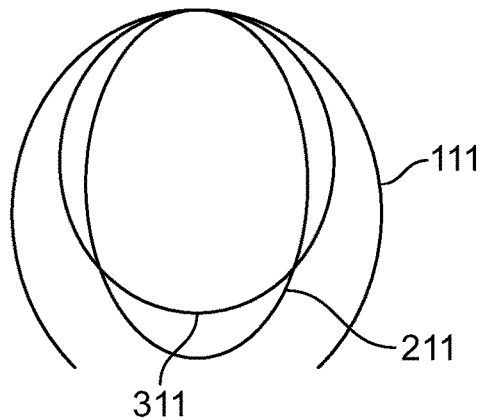
FIG. 6 includes a schematic illustration of three catheter types after unpacking from a first pack size.
Figure 7:
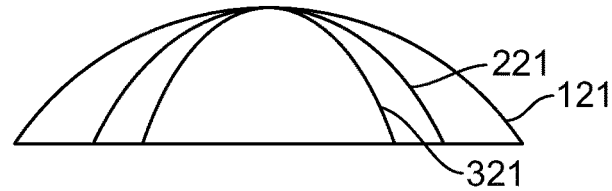
FIG. 7 includes a schematic illustration of three catheter types after unpacking from a second pack size.
Figure 8:
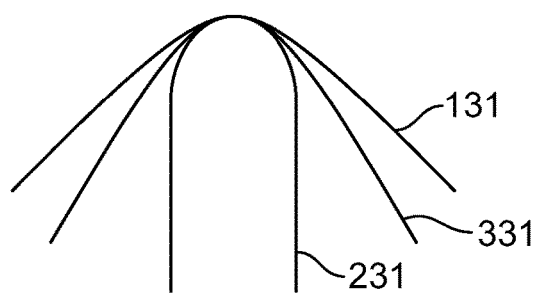
FIG. 8 includes a schematic illustration of three catheter types after unpacking from a third pack size.

FIGS. 6-8 show an illustration of the curvature developed after packing for each of the materials. FIG. 6 shows the results for Pack A TPU tubing 111, TPE tubing 311, and PVC tubing 211. FIG. 7 shows the results for Pack A TPU tubing 121, TPE tubing 221, and PVC tubing 321. FIG. 8 shows the results for Pack A TPU tubing 131, TPE tubing 331, and PVC tubing 231. In all three pack sizes, the TPU material shows better shape recovery than the TPE and PVC material.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:
1. A catheter product comprising:
   a package defining a cavity;
   a catheter including a thermoplastic polyurethane polymer tubing contained within the cavity of the package, wherein at least a portion of the polymer tubing is in a substantially arcuate configuration within the cavity, the portion of the polymer tubing being defined between a proximal location on the polymer tubing and a distal location on the polymer tubing;

wherein a percent shape recovery of the portion of the polymer tubing after about 1 month at room temperature is at least 35%;

wherein the percent shape recovery of the portion of the polymer tubing is calculated by the formula:

percent shape recovery=[1−(L0−L2)/(L0−L1)]×100 where L0=length of the portion of the polymer tubing as measured from the proximal location to the distal location when in a straight configuration;

L1=the diameter of curvature of the portion of the polymer tubing when in the arcuate configuration within the cavity; and L2=the distance between the proximal location and distal location of the portion of the polymer tubing after removal from the arcuate configuration;

wherein the storage modulus (E') of the polymer tubing is greater than or equal to 19 MPa and less than or equal to 50 MPa and the loss modulus (E") of the polymer tubing is greater than or equal to 2.8 MPa and less than or equal to 8.9 MPa.

2. The catheter product of claim 1, wherein the polymer tubing has a shore hardness of at least 80 A.

3. The catheter product of claim 1, wherein the polymer tubing has a shore hardness of between 88 A and 91 A.

4. The catheter product of claim 1, wherein the polymer tubing comprises an annealed polymer tubing.

5. The catheter product of claim 1, wherein the polymer tubing has been annealed for 24 hours at 100 C.

6. The catheter product of claim 1, wherein the polymer tubing comprises polyether thermoplastic polyurethane.

7. The catheter product of claim 1, wherein the polymer tubing comprises an aromatic thermoplastic polyurethane.

8. The catheter product of claim 1, wherein the polymer tubing comprises a polyether aromatic thermoplastic polyurethane.

9. The catheter product of claim 1, further comprising a hydration medium within the cavity of the package.

10. The catheter product of claim 9, wherein the hydration medium comprises water.

11. The catheter product of claim 1, wherein the catheter tubing has a hydrophilic coating.

12. The catheter product of claim 1, wherein the catheter product has been sterilized with e-beam radiation.

13. The catheter product of claim 1, wherein the package comprises a foil.

14. The catheter product of claim 1, further comprising a sleeve at least partially covering the polymer tubing.

15. The catheter product of claim 1, wherein the catheter is a male urinary catheter.

16. The catheter product of claim 1, wherein the substantially arcuate configuration comprises a substantially coiled configuration.

* * * * *